United States Patent
Robinson

[11] Patent Number: 6,070,457
[45] Date of Patent: Jun. 6, 2000

[54] VISCOMETER

[75] Inventor: Geoffrey Robinson, Spring, Tex.

[73] Assignee: Baker Hughes Incorporated, Houston, Tex.

[21] Appl. No.: 09/036,961

[22] Filed: Mar. 9, 1998

Related U.S. Application Data

[63] Continuation-in-part of application No. 08/656,267, Sep. 9, 1996, Pat. No. 5,763,766.

[30] Foreign Application Priority Data

Dec. 17, 1993 [WO] WIPO ............... PCT/GB93/02575

[51] Int. Cl.$^7$ .................... G01N 33/48; G01N 11/14
[52] U.S. Cl. .................................. 73/54.33; 73/54.28
[58] Field of Search ........................ 73/54.33, 54.28

[56] References Cited

U.S. PATENT DOCUMENTS

| | | | |
|---|---|---|---|
| 1,281,042 | 10/1918 | MacMichael | 73/54.33 |
| 2,354,299 | 7/1944 | Bays | 265/11 |
| 2,796,758 | 6/1957 | Myers et al. | 73/60 |
| 2,957,339 | 10/1960 | Penny et al. | 73/59 |
| 3,292,422 | 12/1966 | Banks | 73/59 |
| 4,175,425 | 11/1979 | Brookfield | 73/59 |
| 4,328,701 | 5/1982 | Mau-Tung et al. | 73/59 |
| 4,347,734 | 9/1982 | Heinz | 73/59 |
| 4,448,061 | 5/1984 | Brookfield | 73/59 |
| 4,488,427 | 12/1984 | Matusik et al. | 73/59 |
| 4,534,209 | 8/1985 | Sanders | 73/59 |
| 4,557,142 | 12/1985 | Hensley et al. | 73/153 |
| 4,765,180 | 8/1988 | Clifton | 73/59 |
| 5,201,214 | 4/1993 | Sekiguchi et al. | 73/54.35 |
| 5,287,732 | 2/1994 | Sekiguchi | 73/54.33 |
| 5,763,766 | 6/1998 | Robinson | 73/54.33 |

FOREIGN PATENT DOCUMENTS

| | | |
|---|---|---|
| 79 10915 | 4/1979 | France . |
| 35 31 976 | 9/1985 | Germany . |

*Primary Examiner*—Sandra O'Shea
*Assistant Examiner*—J. David Wiggins
*Attorney, Agent, or Firm*—Duane, Morris & Heckscher LLP

[57] ABSTRACT

The invention comprises a viscometer for indicating a liquid viscosity in terms of a measured rotational deflection imparted upon a support structure for supporting a bob within the liquid, which has a bob assembly unit suspended between the fixation points for a torsion wire. The torsion wire runs through a tube, which is connected to the bob. The tube has cutouts so that it may rotate in response to rotations of a cup, in which the bob is disposed. The framework to support the fixation points for the wire is preferably positioned to extend through cutouts in the tube so as not to interfere with rotational movements of the tube. An arm connected to the tube in conjunction with a transducer measures the angular defection of the wire for determination of viscosity for the fluid being examined. The rotational viscometer also comprises a centralizing device for improving the accuracy, stability, reliability and overall performance thereof, where such centralizing device for the bob exerts a symmetric non-contact force, as a magnetic force, on the bob exposed to the liquid under test.

35 Claims, 2 Drawing Sheets

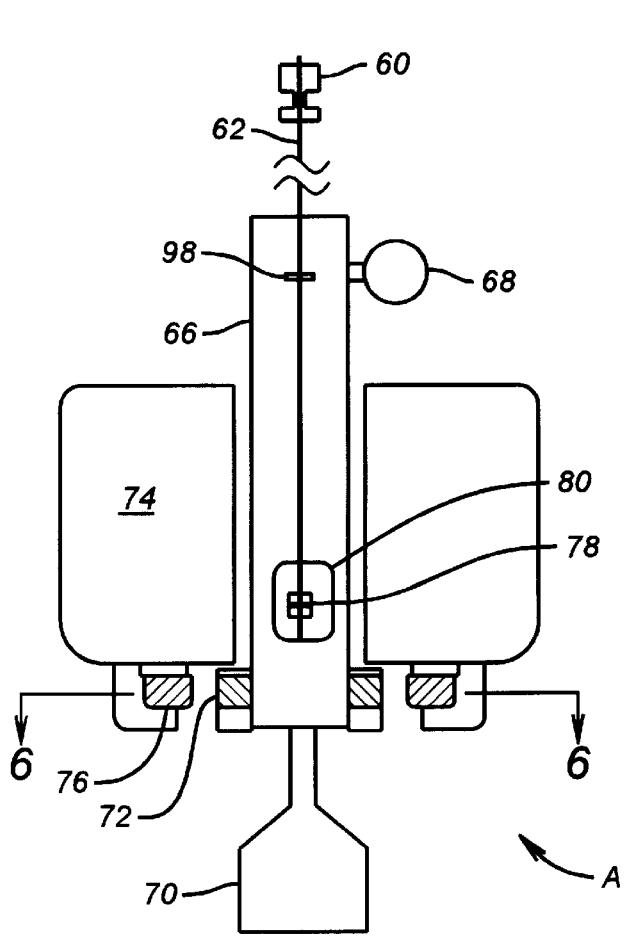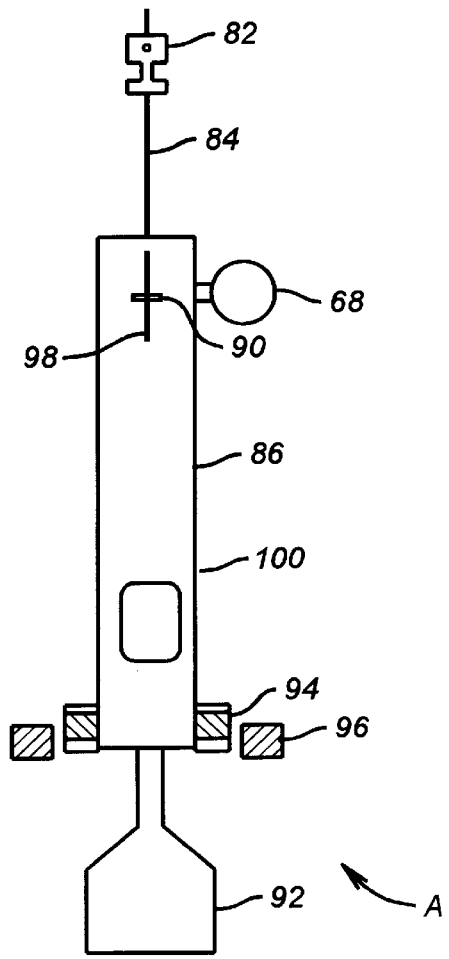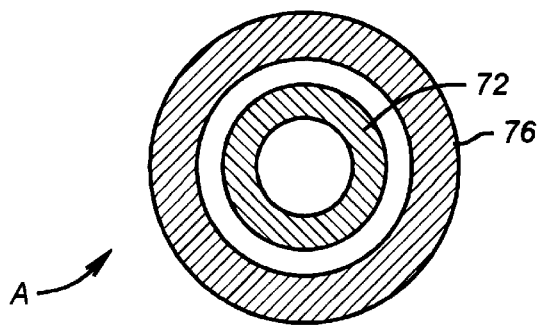
FIG. 4
FIG. 5
FIG. 6

VISCOMETER

Foreign Priority for this U.S. patent application is hereby claimed under 35 U.S.C. 119(b) to PCT international application Number PCT/GB93/02575, as filed Dec. 17, 1993. Also, this application is a continuation-in-part of U.S. Ser. No. 08/656,267 filed Sep. 9, 1996, which became U.S. Pat. No. 5,763,766 dated as Jun. 9, 1998.

FIELD OF THE INVENTION

The field of this invention relates to viscometers, particularly those that require a high degree of accuracy.

BACKGROUND OF THE INVENTION

In prior designs for viscometers, a rotatably mounted container would hold the liquid whose viscosity is to be measured. A pendulum or a "bob" would be supported within the liquid on a wire, and the cylinder holding the liquid would be rotated. The twisting force imparted to the wire holding the bob would then be measured. This twisting force would be used as the basis for measurement of the viscosity of the fluid at a particular temperature. Bobs of the prior designs were generally supported at a single point. These prior designs would use thin wire, ranging from 0.002 to 0.010 inch in diameter, in combination with heavy bobs to keep the bobs centered in the sample when the rotating cup is moving. Other designs involved rods in lieu of thin wires, where the rods had a diameter greater than 0.125 inch. These designs lacked sensitivity because they required extreme forces to impart any twist to them. Yet, other designs, such as U.S. Pat. No. 4,299,118, employed rods in conjunction with a spring coupled to the drive through ball bearings. These types of connections had built-in inaccuracies because even with no sample in the rotating cup, a reading will be obtained when the drive is rotated, simply due to frictional forces between the bob and the rotating cup. The thin wire systems were limited to water and low-viscosity fluids. In the rod systems, inaccuracies occurred because the detection and force-measuring devices were not necessarily linear for the sample in the speed range of interest and because of bearing friction due to the mechanical method of construction.

Prior viscometers of the types discussed above are illustrated in U.S. Pat. Nos. 3,435,666; 1,281,042; 1,192,861; 1,236,706; 2,203,132; 2,303,162; 2,398,574; 2,957,339; and 4,242,086; European Patent Application Nos. 384,792; 007, 427; 311,301; and 449,586; PCT Application Nos. WO92/10736; WO91/14168; and WO91/06364. Other relevant patents in the viscometer art include U.S. Pat. Nos. 4,299, 119 and 3,435,665; and PCT Application No. WO92/06365.

While the prior designs described principally involved suspension of a bob in a cantilevered manner from a single or multiple suspension points, one prior design has incorporated suspension of the bob from a point removed from the fixation points for the torsion wire. In U.S. Pat. No. 2,796,758, the rotating cup 17 is specially constructed to have a U-shaped trough around its periphery. The torsion wire extends through the rotating cup and is fixed above and below the cup. The bob is, in turn, fixed to the torsion wire between the fixation points for the torsion wire. However, the readings of actual torsional displacement of the wire are taken adjacent the uppermost fixation point and not off the bob. A baseline system involving a target mounted to the bob for a neutral reading is used. Thereafter, a disc has to be physically rotated adjacent a fixation point until the indicator connected to the bob is again realigned with the target used to determine the initial position.

The apparatus of the present invention represents an improvement over the viscometer designs of the prior art, and, in particular, the Myers U.S. Pat. No. 2,796,758. The apparatus of the present invention involves a use of a standard rotating cup, rather than a specially designed cup, as used in Myers. The apparatus of the present invention provides multiple fixation points for the torsion wire, coupled with a suspension point for the bob assembly unit between the fixation points. In a preferred embodiment, only a single fixation point is used and tension is applied to the wire by virtue of concentric magnets which also centralize the bob. Both fixation points are aligned above the rotating cup so that standard cup geometries can be used. By fixing the bob as described, first-order inaccuracies due to deflection from a swinging bob are eliminated. Instead, the bob becomes self-centering through the use of the magnets, producing deflection inaccuracies of only the second order. The apparatus of the present invention is more sensitive because it can take the readings of deflection closer to the mid-point of the wire and further from either points of fixation. Using the magnets, the bob assembly can be suspended from different points on the wire without sacrificing accuracy. The apparatus of the present invention takes a direct readout of the rotation of the torsion wire and, through the use of electronic transducers to determine the amount of twist, eliminates another factor of human error in relying on visible deflections read off of an adjacent scale. The apparatus of the present invention involves simple and quick change-out of bobs with minimal effects on accuracy due to such change-outs.

SUMMARY OF THE INVENTION

The invention comprises a viscometer which has a bob assembly unit suspended from a fixation point for a torsion wire. The torsion wire is affixed to the bob. The tube rotates in response to rotations of a cup in which the bob is disposed. A frame with magnets surrounds a tube which supports the bob. The magnets on the frame and tube put the wire in tension and centralize the rotational movements of the bob. An arm connected to the tube in conjunction with a transducer measures the angular defection of the wire for determination of viscosity for the fluid being examined.

BRIEF DESCRIPTION OF THE DRAWINGS

FIG. 4 is a schematic elevational view of an improved design supporting the wire in two places and centralizing the bob with magnets.

FIG. 5 is the preferred embodiment, showing magnets to tension the wire and centralize bob movements.

FIG. 6 is a section view along lines 6—6 of FIG. 4.

DETAILED DESCRIPTION OF THE PREFERRED EMBODIMENT

Figure 1:
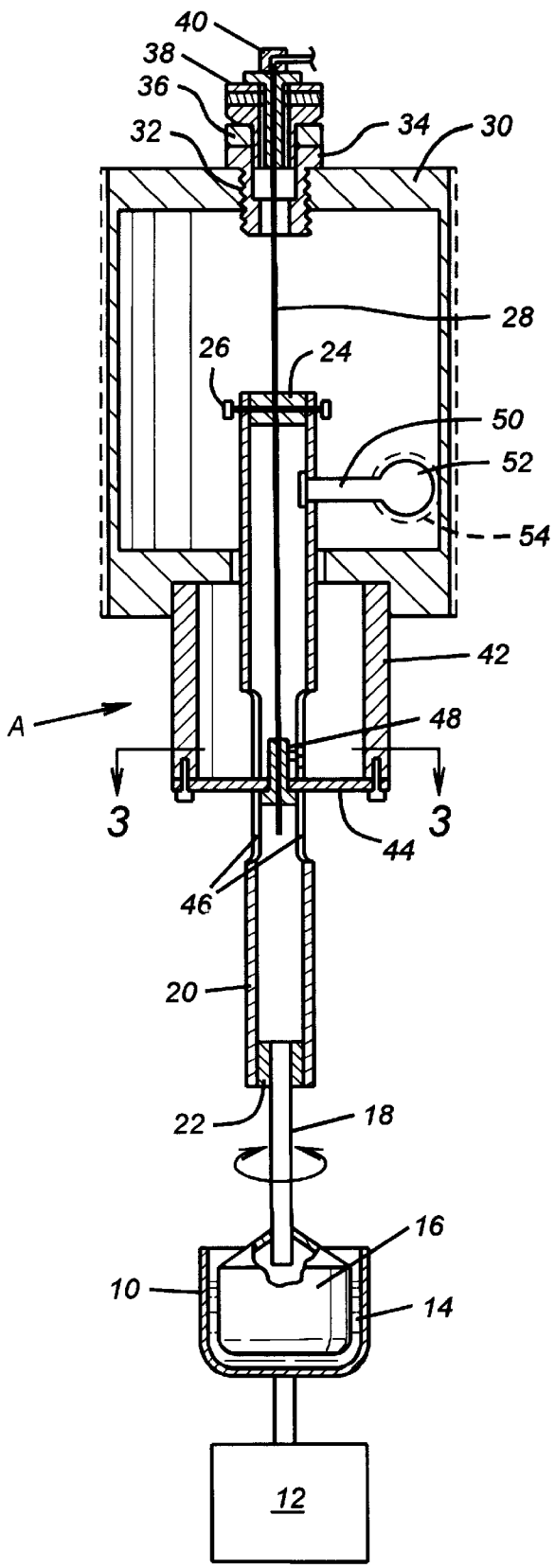
FIG. 1 is a schematic illustration of one embodiment of the apparatus and method of the present invention showing the assembly of the components and their relative positions.
Figure 2:
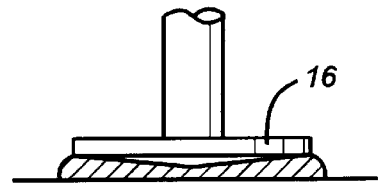
FIG. 2 is an alternate embodiment of the bob of the present invention using a tapered cone configuration.

One version of the apparatus A is shown in FIG. 1. FIG. 5 is the preferred embodiment. In FIG. 1, a container 10 is schematically shown as operably connected to a drive 12 which supports container 10 and rotates it a preselected speed. The container 10 may be of any desired volume and the preferred shape is cylindrical. A fluid 14 whose viscosity is to be determined is deposited in container 10. A bob 16 is positioned in the fluid 14 stored in container 10. As will be described below, the support assembly for the bob can be adjustable so as to allow insertion and extraction of bob 16 from a container 10. Alternatively, container 10 may be so situated with respect to drive 12, which could optionally include a rotary table, so as to allow positioning of the bob 16 within the container 10 by movement of container 10 or its underlying support structure, shown schematically as drive 12. In the preferred range, drive 12 can be a variable-speed drive or a drive capable in other ways of delivering several preselected speeds, preferably ranging in the order of about 0.01 RPM up to about 1000 RPM.

Bob 16 may be a cylinder shape or it can be a flat plate used in conjunction with a container 10 which itself can be another flat plate. Bob 16 may have a taper, with 4° or less being preferred if such type of bob 16 is used. A cylinder shape is also preferred and can be of service for a wider variety of fluids.

Extending from bob 16 is shaft 18 which is preferably connected to a tube 20. Tube 20 moves in tandem with shaft 18 and bob 16. Shaft 18 is connected to tube 20 at its lower end 22. At upper end 24, a fixation device 26 is disposed for the purpose of fixing tube 20 to wire 28. Wire 28 is fixed in two points. The first point is on housing or frame 30. Housing 30 has preferably a threaded bore 32 to which is mounted an adjustment nut 34. Above the adjustment nut 34 is a lock nut 36, which works in conjunction with a centralizer 38 to complete the upper attachment point of wire 28. Wire 28 has a projection 40 at its end which engages centralizer 38 to trap the upper end of wire 28. The lower end of wire 28 is fixed indirectly to housing or frame 30. Housing 30 has a lower extension 42 characterized by a mounting bar 44. The mounting bar 44 extends through tube 20 through a slot 46. Mounted centrally on the mounting bar 44 is wire attachment 48. The attachment 48 can be any one of a variety of different mechanical attachments and is preferably releasable. The slots 46 are sufficiently wide to allow tube 20 to rotate along its longitudinal axis in response to a torque transmitted through the fluid 14 into bob assembly unit 16, resulting from drive 12 turning container 10. It is easy to see that the fixing point for the bob assembly unit 16 occurs between the upper fixation point at projection 40 and the lower attachment point at wire attachment 48. By turning the adjustment nut 34, the slackness in the wire 28 can be removed. The preferred material for wire 28 is a Phosphor Bronze Alloy with the thickness of the wire being dependent on the viscosity of the fluid being measured. Higher viscosity fluids allow for the use of thicker wires. For example, wire diameter ranges of 0.030–0.850 inch can be used with anticipated viscosities of the drilling fluids (10 centipoise (cp)–1000 poise (p)). In the preferred embodiment, drive 12 can rotate container 10 at preselected speeds which can vary as low as about 0.01 RPM to a maximum speed of in excess of 600 RPM. Rotation of container 10 resulting from operation of drive 12 induces a torque on the bob 16 which, in turn, induces tube 20 to rotate. Mounted to tube 20 close to the fixation point at the upper end 24 of tube 20 is arm 50 which, at its end, has transducer-sensing pad 52. A transducer schematically shown as 54 senses the amount of movement of sensing pad or target 52 so that the measurement of angular deflection can be determined electronically.

In view of the techniques for mounting the bob 16, it can readily been seen that bobs can quickly be replaced or that the wire 28 can be replaced, as needed, to accommodate testing of fluids of different viscosities.

Significantly, to improve sensitivity, the fixation point for bob 16 to the wire 28 occurs between the ends of wire 28. The fixation point at the upper end 24 of tube 20 occurs about midway on wire 28 between attachment 48 and projection 40. Further, the take-off point for a deflection measurement is also adjacent the fixation point between the tube 20 and the wire 28. Again, this reduces measurement errors by increasing sensitivity since the deflection is measured at a point on the wire that is most likely to twist correspondingly to the amount of applied torque from the fluid 14 onto bob 16, resulting from rotation of container 10 by drive 12. Through the use of electronic transducers, the precise movement of target 52 is determined electronically, thus further reducing human errors inherent in some of the prior designs which required manual contact, visual observation, or judgment by a test operator.

The apparatus of the present invention facilitates use of standardized containers 10 and does not require complex containers, such as those disclosed in U.S. Pat. No. 2,796,758, which has a fixation point for the wire below its rotating container. In the apparatus of the present design, a readout of the amount of twist of tube 20 is made directly and through a transducer, further eliminating errors due to indirect measurements, such as those employed in U.S. Pat. No. 2,796,758.

Since the wire 28 can be tensioned between two points, it is in effect centralized. This eliminates the need as in the prior designs for relying on very thin wires and heavy bobs to keep the bob centered in the sample when the cup holding the sample is being rotated.

The mounting method illustrated in FIG. 1 also lends itself to great linearity in a broader range of speeds than those devices of the prior art where linearity was particularly problematic at low speeds. The drive 12 could also be arranged to be sinusoidal in order to provide true gel characteristics of the sample. Sinusoidal drive involves a continuous change of direction at a predetermined speed after rotation of a particular distance. This back and forth action is especially useful with sensitive fluids where continuous rotation in a single direction can affect the fluid properties.

The use of the mounting system, as illustrated in FIG. 1, for the wire 28 also allows use of lower clearances between bob 16 and the container 10. Sample volumes can be reduced and measuring accuracy is improved through the use of a lower clearance made possible by the mounting method which effectively centralizes bob 16. The apparatus A of the present invention shown in FIG. 1 makes it possible to achieve a ratio of bob-to-cup diameter of 0.96 or greater. In prior designs, this has been a problem due to lack of a centralizing effect on the bob found in prior designs.

Figure 3:
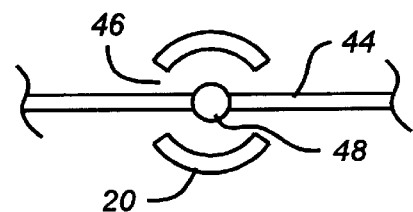
FIG. 3 is a section view along lines 2—2.

FIG. 4 represents an improvement over the embodiment illustrated in FIG. 1. FIG. 4 is schematic, showing a nut 60 which is connected to a frame (portions of which are not shown) to fixate the upper end of the wire 62. Wire 62 extends to a fixation point 64. Fixation point 64 secures the tube 66 which has with it target 68. The tube 66 supports the bob 70. Tube 66 has one or more magnets 72 arranged in a generally circular pattern, as illustrated in FIG. 6. The portion of the frame 74 is illustrated and it supports a magnet or magnets 76, which generally form a concentric circle or pattern to magnets 72. The wire 62 is fixated at a point 78 to the frame 74 through windows 80 in a similar manner as shown in FIGS. 1 and 3. In essence, the embodiment illustrated in FIG. 4 is similar to the embodiment shown in FIG. 1 in the manner that the wire is supported. The significant difference in the embodiment of FIG. 4 is that the frame 74, with its magnets 76 which are concentric with magnets 72 connected to tube 66 and not longitudinally offset as in FIG. 5, provide a centralizing force on the bob 70 without in any way retarding its ability to turn responsive to movements of a fluid-laden cup which is being rotated (not shown but see FIG. 1) where the fluid contacts the bob. The improvement in the FIG. 4 design over the FIG. 1 design is that in certain locations such as offshore where, due to wave action, there is movement of the structure which supports the frame 74, the centralizing effect provided by the magnets 72 and 76 enhances the performance of the apparatus A. Movements of offshore rigs will not affect the sensitivity of the instrument in that the bob 70 will remain centralized within the surrounding cup, despite movements of the support structure on which the frame 74 is located.

While a magnetic field using magnets is preferred, the invention comprises any technique to centralize the bob without contact since contact would affect the accuracy of the viscometer.

The embodiment of FIG. 5 represents the currently known preferred embodiment. It utilizes an upper support 82 for the wire 84. The upper support 82 is affixed to a frame (which is not shown). The tube 86 has a target 88 and is affixed to the wire 84 at fixation point 90. Tube 86 supports bob 92. Tension in wire 84 comes from the interplay of magnets 94 with magnets 96. The arrangement of the magnets 94 and 96 is identical to the magnet arrangement shown in FIG. 4 for magnets 72 and 76, with the distinction being that the magnets 94 and 96 are offset in transverse planes with respect to the wire 84. Due to the polarity of the magnets 94 and 96 causing them to repel each other, not only is a centralizing effect provided for the tube 86, but also a downward force tending to put tension in wire 84 results from the juxtaposition of magnets 94 and 96. Accordingly, the wire 84 has an end 98 which does not extend as far as window 100. In effect, the pairs of magnets 94 and 96 provide, without physical contact, the counterpart to the lower fixation point 78, shown in FIG. 4. The embodiment in FIG. 5 is also beneficial when the apparatus A is used in offshore applications or in any other conditions where vibrations or wave action is present. The bob 92 remains centralized within the spinning cup (not shown) due to the interplay of the magnets 94 and 96. Additionally, the wire 84 remains taut and the need for a lower fixation point for the wire 84 become unnecessary as the downward force applied from the interplay of magnets 94 and 96 keeps the wire 84 in a taut condition. Thus, the desirable benefits of the apparatus A, which have been previously described for the embodiment of FIG. 1, are all present in the embodiments of FIGS. 4 and 5. In the preferred embodiment of FIG. 5, the construction of the apparatus A is greatly simplified and made more reliable in hostile environments.

The combination of centralization and applying a tensile force on the wire in the preferred embodiment can be accomplished by other techniques which could involve use of other types of fields or any other noncontacting technique.

The foregoing disclosure and description of the invention are illustrative and explanatory thereof, and various changes in the size, shape and materials, as well as in the details of the illustrated construction, may be made without departing from the spirit of the invention.

I claim:

1. A viscometer for indicating a liquid viscosity in terms of a measured rotational deflection imparted upon a support structure that supports a bob within the liquid, comprising:

a frame supporting a wire in tension between at least two locations;

a bob connected to said wire at at least one fixation point between said two locations; and a centralizing device located adjacent to said bob, said centralizing device exerting a symmetric force on said bob in a direct non-contact manner.

2. The viscometer of claim 1, wherein:

said centralizing device makes no contact with said bob.

3. A frame supporting a wire in at least two locations;

a bob connected to said wire between said two locations;

a centralizing device for said bob supported at least in part from said frame;

said centralizing device makes no contact with said bob;

said centralizing device employs a magnetic field.

4. The viscometer of claim 3, wherein:

said centralizing device comprises at least one first magnet mounted on said frame;

said bob comprises at least one second magnet in proximity to said first magnet so that said magnets repel each other.

5. The viscometer of claim 4, wherein:

said first and second magnets are annularly shaped and said second magnet is disposed within said first magnet.

6. The viscometer of claim 5, wherein:

said first and second magnets are concentric and are in general alignment in a plane perpendicular to said wire.

7. The viscometer of claim 2, further comprising:

a rotatable container to hold a sample fluid whose viscosity is to be measured as said container is rotated and said bob is in contact with the fluid;

a noncontact measurement device to measure the degree of bob rotation responsive to a torque applied to said bob from the fluid.

8. The viscometer of claim 6, wherein:

a rotatable container to hold a sample fluid whose viscosity is to be measured as said container is rotated and said bob is in contact with the fluid;

a noncontact measurement device to measure the degree of bob rotation responsive to a torque applied to said bob from the fluid.

9. The viscometer of claim 6, wherein:

said support wire is connected to said frame at an upper and a lower mounting point, both disposed on the same side of said container.

10. The viscometer of claim 9, wherein:

said bob further comprises an elongated extension spanning over said lower mounting point;

said extension connected to said support wire at said point of fixation for support of said bob by a fixation device;

said extension rotatable with respect to said lower mounting point of wire without contact therewith.

11. The viscometer of claim 10, wherein said measurement device further comprises:

an arm extending from said extension;

a sensor for detecting angular movement of said arm responsive to torque applied to said bob from the fluid being tested during rotation of said container.

12. The viscometer of claim 11, wherein:

said arm extends radially from said extension and further comprises a target;

said sensor disposed adjacent said target for determination of the amount of movement of said target.

13. The viscometer of claim 10, wherein:
said extension of said bob is mounted to said wire at a point of fixation about midway between said upper and lower mounting points.

14. The viscometer of claim 13, wherein:
said measurement device is disposed on said extension of said bob close to its said point of fixation to said support wire.

15. The viscometer of claim 9, wherein:
said frame comprises a plurality of spokes to support said lower mounting point;
said extension comprising a plurality of cutouts, each said spoke extending through a corresponding said cutout to allow said bob rotational freedom with respect to said frame, which remains fixed.

16. A frame supporting a wire in at least two locations;
a bob connected to said wire between said two locations;
a centralizing device for said bob supported at least in part from said frame;
said centralizing device makes no contact with said bob;
a rotatable container to hold a sample fluid whose viscosity is to be measured as said container is rotated and said bob is in contact with the fluid;
a noncontact measurement device to measure the degree of bob rotation responsive to a torque applied to said bob from the fluid;
said rotatable container can vary in speed between about 0.01 RPM to about 1000 RPM.

17. A frame supporting a wire in at least two locations;
a bob connected to said wire between said two locations;
a centralizing device for said bob supported at least in part from said frame;
said centralizing device makes no contact with said bob;
a rotatable container to hold a sample fluid whose viscosity is to be measured as said container is rotated and said bob is in contact with the fluid;
a noncontact measurement device to measure the degree of bob rotation responsive to a torque applied to said bob from the fluid;
the ratio of diameters of said bob to said container is about 0.96 or greater.

18. A frame supporting a wire in at least two locations;
a bob connected to said wire between said two locations;
a centralizing device for said bob supported at least in part from said frame;
said centralizing device makes no contact with said bob;
a rotatable container to hold a sample fluid whose viscosity is to be measured as said container is rotated and said bob is in contact with the fluid;
a noncontact measurement device to measure the degree of bob rotation responsive to a torque applied to said bob from the fluid;
said container and the lower portion of said bob are substantially flat, with said bob having an inclined surface varying up to about a 4° taper.

19. A viscometer for indicating a liquid viscosity in terms of a measured rotational deflection imparted upon a support structure that supports a bob within the liquid, comprising:
a frame supporting a wire in tension between at least two locations;
a bob supported by said wire at at least one fixation point between said two locations; and
a centralizer, located adjacent to said bob, which applies a symmetric force to said bob in a direct non-contact manner.

20. The viscometer of claim 19, wherein:
said wire is supported from said frame at a single location;
said centralizer applies a tensile force to said wire.

21. The viscometer of claim 19, wherein:
said centralizer does not impede rotational movement of said bob.

22. The viscometer of claim 20, wherein:
said centralizer does not impede rotational movement of said bob.

23. The viscometer of claim 20, wherein:
said centralizer employs a force field to put a tensile force on said wire through said bob.

24. A viscometer, comprising:
a frame supporting a wire;
a bob supported by said wire;
said frame supporting a centralizer for said bob;
said wire is supported from said frame at a single location;
said centralizer applies a tensile force to said wire;
said centralizer employs a force field to put a tensile force on said wire through said bob;
said centralizer comprises magnets on said frame and said bob which repel each other to create a tensile force on said wire.

25. The viscometer of claim 24, wherein:
said magnets are nested so as to employ the repelling between them to centralize said bob.

26. The viscometer of claim 21, wherein:
said centralizer employs a force field which spans a gap between said frame and said bob.

27. A viscometer, comprising:
a frame supporting a wire;
a bob supported by said wire;
said frame supporting a centralizer for said bob;
said centralizer does not impede rotational movement of said bob;
said centralizer employs a force field which spans a gap between said frame and said bob;
said centralizer employs nested magnets on said frame and bob, respectively, which form said magnetic field and repel each other to centralize said bob.

28. The viscometer of claim 27, wherein:
said magnets are offset so as to put a tensile force on said wire by inducing a downward force on said bob through said field.

29. The viscometer of claim 19, wherein:
a rotatable container to hold a sample fluid whose viscosity is to be measured as said container is rotated and said bob is in contact with the fluid;
a noncontact measurement device to measure the degree of bob rotation responsive to a torque applied to said bob from the fluid.

30. The viscometer of claim 29, wherein said measurement device further comprises:
an arm extending from an extension on said bob;
a sensor for detecting angular movement of said arm responsive to torque applied to said bob from the fluid being tested during rotation of said container.

31. The viscometer of claim 30, wherein:
said arm extends radially from said extension and further comprises a target;
said sensor disposed adjacent said target for determination of the amount of movement of said target.

32. The viscometer of claim 30, wherein:

said measurement device is disposed on said extension of said bob close to its said point of fixation to said support wire.

33. A viscometer, comprising:

a frame supporting a wire;

a bob supported by said wire;

said frame supporting a centralizer for said bob;

a rotatable container to hold a sample fluid whose viscosity is to be measured as said container is rotated and said bob is in contact with the fluid;

a noncontact measurement device to measure the degree of bob rotation responsive to a torque applied to said bob from the fluid;

said rotatable container can vary in speed between about 0.01 RPM to about 1000 RPM.

34. A viscometer, comprising:

a frame supporting a wire;

a bob supported by said wire;

said frame supporting a centralizer for said bob;

a rotatable container to hold a sample fluid whose viscosity is to be measured as said container is rotated and said bob is in contact with the fluid;

a noncontact measurement device to measure the degree of bob rotation responsive to a torque applied to said bob from the fluid;

the ratio of diameters of said bob to said container is about 0.96 or greater.

35. A viscometer, comprising:

a frame supporting a wire;

a bob supported by said wire;

said frame supporting a centralizer for said bob;

a rotatable container to hold a sample fluid whose viscosity is to be measured as said container is rotated and said bob is in contact with the fluid;

a noncontact measurement device to measure the degree of bob rotation responsive to a torque applied to said bob from the fluid;

said container and the lower portion of said bob are substantially flat, with said bob having an inclined surface varying up to about a 4° taper.

* * * * *